US005958266A

United States Patent [19]
Fugo et al.

[11] Patent Number: 5,958,266
[45] Date of Patent: Sep. 28, 1999

[54] METHOD OF PLASMA INCISION OF MATTER WITH A SPECIFICALLY TUNED RADIOFREQUENCY ELECTROMAGNETIC FIELD GENERATOR

[76] Inventors: Richard J. Fugo; Damian Coccio, both of 1507 Plymouth Blvd., Norristown, Pa. 19401

[21] Appl. No.: 08/957,786

[22] Filed: Oct. 24, 1997

[51] Int. Cl.$^6$ ................................ A61N 5/00; B23K 9/00
[52] U.S. Cl. ................. 219/121.59; 606/32; 219/121.52
[58] Field of Search ......................... 219/121.52, 121.59; 606/32–52

[56] References Cited

U.S. PATENT DOCUMENTS

| | | | |
|---|---|---|---|
| 3,663,858 | 5/1972 | Lisitano | 315/39 |
| 4,599,134 | 7/1986 | Babu | 156/626 |
| 4,691,090 | 9/1987 | Garlanov | 219/121 PC |
| 4,855,563 | 8/1989 | Beresnev | 219/121.39 |
| 5,108,391 | 4/1992 | Flachenecker | 606/38 |
| 5,217,457 | 6/1993 | Delahuerga | 606/42 |
| 5,235,155 | 8/1993 | Yamada | 219/121.39 |
| 5,300,068 | 4/1994 | Rosar | 606/34 |
| 5,346,491 | 9/1994 | Oertli | 606/37 |
| 5,558,671 | 9/1996 | Yates | 606/38 |
| 5,591,301 | 1/1997 | Grewal | 156/643.1 |
| 5,599,344 | 2/1997 | Paterson | 606/34 |
| 5,628,745 | 5/1997 | Bek | 606/38 |
| 5,647,869 | 7/1997 | Goble | 606/37 |
| 5,669,907 | 9/1997 | Platt | 606/48 |
| 5,669,975 | 9/1997 | Ashtiani | 118/723 |

OTHER PUBLICATIONS

Dull, Charles E. et al, "Modern Physics". Henry Holt & Co. pp. 526–541, 1960.
Newman, James R., ed. "The Harper Encyclopedia of Science" Harper and Row Publishers, pp. 923–924, 1967.
Newman, James R., ed. "The Harper Encyclopedia of Science" Harper and Row Publishers, pp. 697, 1967.
Milner, D.R. et al., "Introduction to Welding and Brazing" Pergamon Press, pp. 64–83, 1968.
Friedman, Joshua, "The Technical Aspects of Electrosurgery" J. Oral Surgery, vol. 36, No. 2, pp. 177–187, 1973.
Besancon, Robert M. ed., "The Encyclopedia of Physics" 2nd ed. Van Nostrand Reinhold Co., pp. V–XIII;851–853, 1974.
Sozio, Ralph B. et al., A Histologic & Electronic Evaluation of Electrosurgical Currents: Non–filtered full–wave modulated vs. Filtered Current. J. of Prosthetic Dentistry pp. 300–311, Mar. 1975.
Maness, W.L. et al. "Histologic evaluationof electrosurgery with varying frequency and waveform" J. of Prostetic Dentistry, vol. 40, No. 3 pp. 304–308, 1978.
Krause–Hohnestein, U. "Electrosurgery: Fundamental Requirements for Use" Quintessense Intn'l Nov. 1983, pp. 1115–1124.
Chen, Francis F., "Introduction to Plasma Physics & Controlled Fusion" Plwnum Pub. Co., pp. I–XV, 1–17, 1983.
Ichimaru, Setsuo, "Statistical Plasma Physics vol. I: Basic Principles" Addison Wesley Pub Co, pp. 323–359, 1992.
Ichimaru, Setsuo, Statistical Plasma Physics vol. I: Basic Principles Addison Wesley Pub Co, pp. I–XiX, 1–28, 1992.
Ferris, Daron G. et al. Gynecologic & Dermatologic Electrosurgical Units: A comparative review. J. of Family Practice vol. 39, No. 2, pp. 160–169, 1994.
The Lincoln Electric Co. "The Procedure Handbook of Arc Welding 13th ed". pp. 1.3–1 to 1.3–4, 1994.
Atkins, Peter "Physical Chemistry 5th ed" W.H. Freeman & Co. pp. 400–402, 1994.
Nishikawa, K. "Plasma Physics: Basic Theory with FUsion Applications" Springer=Verlay, pp. V–XIII, 1–55, 1994.
Goldston, Robert J, et al. "Intro to Plasma Physics" Inst. of Physics Publishing pp. 132–135, 1995.
Ellman Surgitron FFPF + Surgitron Operating Manual pp. 1–10.

*Primary Examiner*—Cary O'Connor
*Assistant Examiner*—Michael Astorino

[57] ABSTRACT

A method of incising matter with a harmonious plasma cloud. An inexpensive radiofrequency generator and power amplifier generates an electromagnetic wave which is transmitted from an incising transmitter probe. This electromagnetic wave is impedance matched, frequency matched, and power matched to initiate and sustain a harmonious plasma cloud with low atomic particle turbulence and chaos. This harmonious plasma cloud forms a coating over the surface of the incising tip as well as acts to reduce the energy output needed from the power amplifier. The electromagnetic wave is also used to produce a Pinch Effect to compress, contour, shape and control the harmonious plasma cloud. The electromagnetic wave is furthermore used to trap and contain the plasma cloud without the need of a solid matter containment vessel according to the Magnetic Bottle Effect of physics. The Tunnelling effect of physical chemistry is utilized to amplify the energy delivered to the harmonious plasma cloud while shielding matter surrounding the intended path of incision from potential radiation exposure. The system provides an efficient, effective, safe, clean and inexpensive approach to producing an incision in matter.

18 Claims, No Drawings

METHOD OF PLASMA INCISION OF MATTER WITH A SPECIFICALLY TUNED RADIOFREQUENCY ELECTROMAGNETIC FIELD GENERATOR

BACKGROUND

1. Field of Invention

This invention relates to incisions placed in matter with a harmonious plasma cloud, specifically to harmonious plasma clouds initiated and sustained by electromagnetic energy waves transmitted from a radiofrequency signal generator system which is impedance matched, frequency matched and output power matched to the atomic particles comprising the harmonious plasma cloud that coats the activated transmitter incision probe.

2. Description of Prior Art

Most incisions made are created with a hardened physical blade, such as a steel blade, a sapphire blade, or a diamond blade. Such incisions are based on frictional physical interactions of a sharp, acute edge of hardened matter against a surface of the matter to be incised. Such purely physical methods of one hardened matter attempting to cut through another hardened matter are inefficient and therefore experience significant frictional resistance and inefficiencies when the matter being incised is extremely solid and dense. For these reasons, others have resorted to methods such as electronically generated incisions, electro-incisions or electrosurgery of matter. With this form of approach to incision of matter, electrical arcs induce arc burns or volatilization of matter while electrical ohmic resistance in the matter to be incised creates a heating effect due to phenomenon such as dielectric hysteresis and eddy currents. These last two phenomenon produce an effect known as diathermy which may result in a physical reaction that can produce a cutting effect in matter. This approach has received limited use since it's shortcomings include extensive damage to matter outside of the intended incision path, with the resultant production of burning, charring and frequently unpleasant smelling fumes. The inefficiency of classic electro-incision units is manifested by the high power needed to produce a cutting effect at the incising tip, usually in excess of 50 watts of power. This relatively high power output needed in classic electro-surgical or electro-cutting units is secondary to the cutting inefficiency of these units which operate on a combination of classic ohmic diathermy and unstable, caustic plasma arcing.

Lasers have also been used to incise and cut; however, these units are expensive and require a large amount of system input energy to create a laser beam with sufficient power to cut or make an incision into matter. Lasers have been used to generate plasma and are used in processing such as etching in the field of microelectronics.

Plasma arcing can be found in a number of areas such as welding arcs, spark plug arcs, lightning bolt arcs, neon lights and electrosurgical arcs. Arcing, per se, is a form of disharmonious plasma flow and represents uncontrolled, turbulent flow of ionized atomic particles in plasma as well as increased atomic particle chaos in the plasma. The atomic particle turbulence in plasma arcs represents a form of atomic particle chaos and the uncontrolled nature of the atomic particle chaos causes a large quantity of energy spillover into matter outside of the intended path of incision and thereby may produce exessive heating. This energy spillover into matter surrounding the intended path of incision into matter results in energy exposure and damage to surrounding matter. Merely reducing the cutting tip power does not by itself significantly improve the plasma harmony in as much as it does not greatly decrease the flow turbulence of the ionized atomic particles that make up a plasma arc. Moreover, our invention uses an array of physical chemistry principles to minimize disharmonious plasma arcing. Our invention minimizes disharmonious plasma arcing by minimizing the atomic particle turbulence in the plasma cloud thereby greatly reducing the plasma cloud atomic particle chaos and thereby creating a harmonious plasma cloud. Harmonious plasma cuts in a more controlled, efficient and safer manner because the atomic particle components in a harmonious plasma cloud exist in a more stable, balanced, and controlled state with a higher order of organization and less atomic particle turbulence than disharmonious plasma. Our harmonious plasma cloud is furthermore compressed, controlled, contoured and shaped by utilizing the Pinch Effect of physics. Our compressed plasma cloud is then trapped and contained by the Magnetic Bottle phenomenon well known to physicists and employed in fields such as nuclear physics.

SUMMARY OF THE INVENTION

Our invention is a method of creating a harmonious plasma cloud with low turbulence of atomic particles in the plasma cloud, thereby representing a state of low atomic particle chaos in the plasma. Physics defines four types of matter: solids, liquids, gases and plasma. Although examples of plasma are uncommon on earth, the majority of the universe is comprised of plasma. Our form of plasma cloud is generated by an inexpensive radiofrequency generator and amplifier similar to a standard, commercial radio transmitter. The low input energy requirement of our electromagnetic generator system is partially made possible by impedance matching, frequency matching, and system output power matching the incising transmitter probe to the harmonious plasma cloud. The activated transmitter incising tip creates a plasma cloud which then forms a coating over the surface of the activated transmitter incising tip. Our incising transmitter probe is preferably a solid, non-hollow conductor, but a hollow incising transmitter probe may also be used. When our radiofrequency electromagnetic transmitter is activated, the majority of electron flow occurs along the surface or skin of the incising transmitter or cutting tip, according to the Skin Effect of physics. By impedance matching the radiofrequency electromagnetic wave of the activated incising transmitter tip to the plasma cloud coating the incising electrode tip, we produce a tightly coupled energy transfer system wherein a high percentage of total electromagnetic energy is transmitted into the plasma cloud whereas only a small percentage of the total electromagnetic energy is reflected back into the activated transmitter incising probe. This concept is analogous to impedance matching a standard radio transmitter antennae to atmospheric air.

Arcing, per se, is a form of disharmonious plasma flow and represents uncontrolled, turbulent flow of ionized atomic particles in plasma that results in increased atomic particle chaos in the plasma. Merely reducing the cutting tip power does not, however, significantly improve the plasma harmony in as much as it does not greatly decrease the flow turbulence of the ionized atomic particles that make up a plasma arc. The atomic particle turbulence in plasma arcs represents a form of atomic particle chaos and the uncontrolled nature of the atomic particle chaos causes a large quantity of energy spillover into matter outside of the intended path of incision and thereby may produce excessive heating. This energy spillover into matter surrounding the intended path of incision into matter results in thermal exposure and radiation exposure with resultant damage to surrounding matter. Moreover, our invention minimizes plasma arcing by minimizing the atomic particle turbulence in the plasma cloud thereby greatly reducing the plasma cloud atomic particle chaos and thereby creating a harmonious plasma cloud.

Once the harmonious plasma cloud is created, the harmonious plasma cloud may then be compressed, controlled, contoured and shaped by utilizing the electromagnetic wave transmitted from the active incising transmitter tip thereby employing the Pinch Effect of physics. This compressed plasma cloud is then trapped and contained by utilizing the transmitted magnetic field according to the Magnetic Bottle phenomenon well known to physicists and employed in fields such as Nuclear Physics. This allows us to decrease the thickness of the plasma coating covering the incising electrode by compressing, concentrating and trapping the harmonious plasma cloud. This effect thereby allows us to increase the density of the harmonious plasma coating on the incising tip. Increased atomic particle density of the harmonious plasma cloud produces an increased plasma cloud energy density. This therefore allows increased efficiency of incision into matter as well as a thinner path of incision into the matter to be incised. Once our generated electromagnetic wave passes through the plasma coating, it then encounters the matter surrounding the harmonious plasma cloud to which the electromagnetic wave is not well impedance matched. Therefore, a large percentage of total electromagnetic radiation energy is reflected back into the harmonious plasma coating while only a small percentage of the total electromagnetic radiation is transmitted into the surrounding matter. This physical interaction of electromagnetic radiation with matter is described by the Tunnelling effect of physical chemistry. This electromagnetic wave energy which is reflected back into the harmonious plasma cloud acts to further energize the atomic particles of the plasma cloud and thereby further decrease the electromagnetic energy output required by our electromagnetic waveform generator system.

A combination of increased plasma harmony, increased harmonious plasma density, a thinner coating of harmonious plasma on the activated transmitter incising probe, and the Tunnelling Effect on our generated electromagnetic waveform results in a high efficiency, clean incision of matter in the intended path of incision with minimal spillover of energy into matter surrounding the intended path of incision. Decreasing spillover of energy into tissue surrounding the intended path of incision results in a significant reduction of damage to matter outside of the intended path of incision. According to principles of physics, harmonious plasma is formulated to cut and incise matter more efficiently and cleaner than prior modalities of incision.

As opposed to classic electrocuting units, the oscillation frequency of our electromagnetic generator system is tuned to the molecular oscillation harmonics of the plasma cloud along the surface interface of the incising tip and matter to be incised. The kinetic energy level of this thin layer of surface atomic particles becomes extraordinarily high thereby forming a cloud of high energy ions and electrons surrounding the cutting electrode. The molecules in the plasma cloud are then attracted centripetally toward the cutting probe tip by a continuous or pulsed mode radiofrequency wave being fed into the cutting transmitter tip from which an electromagnetic wave is radiated. This effectively creates a highly concentrated coating of harmonious cutting plasma over the surface of the cutting probe. Our invention allows us to create a cutting plasma cloud without injecting ionizable gas into the field of cutting such as occurs in plasma generating devices such as plasma torches and etching systems in plasma chambers. Once the electromagnetic radiation is turned off, the plasma rapidly discharges energy and the atomic particles in the plasma cloud lose the energy needed to remain in the plasma state. By stimulating the electrode tip with radiofrequency energy while impedance matching, frequency matching, and power matching the activated electromagnetic probe to the harmonious plasma cloud coating, a plasma blade may be created which cuts with the energy of the plasma atomic particles. Impedance matching the transmitted electromagnetic radiation to the plasma surrounding the incision tip is similar to impedance matching the electromagnetic radiation from a transmitter antennae into the air surrounding the antennae. Once the electromagnetic wave passes through the layer of plasma, it passes into matter not in the intended incision path and encounters matter to which it is not impedance matched causing a high order decay of the transmitted electromagnetic signal in a manner described by the physical chemistry principle of Tunnelling. For these reasons, the efficiency of incision is amplified in the intended path of incision while it is highly damped outside of the intended path of incision, thereby producing minimal electromagnetic radiation exposure, impact or side effects on the matter outside of the path of intended incision. The end result is a safe, clean and efficient incision in matter.

OBJECTIVES AND ADVANTAGES

Accordingly, several objects and advantages of the present invention are:

(a) to provide an incisional method that uses an inexpensive electronic radiofrequency signal generator, amplifier, and transmitter probe to generate, amplify and transmit an electromagnetic wave.

(b) to employ a solid, non-hollow conductive radiofrequency transmitter probe to create, maintain and control plasma. Nonetheless, the transmitter probe may be completely hollow or partially hollow in design.

(c) to produce a plasma cutting blade from an electronic electromagnetic field generator system which requires low system input energy relative to other incisional methods presently in use. Likewise, this system requires lower system output energy relative to other incisional methods presently in use, even as low as 1 watt of average output power.

(d) to create a plasma cloud without injecting an ionizable gas into the field of cutting as is seen in plasma generating devices such as plasma torches and etching systems in plasma chambers.

(e) to create a harmonious plasma cloud with low atomic particle chaos and turbulence by impedance matching the energy from our electromagnetic generator system to the plasma cloud that surrounds and coats the activated incising transmitter tip electrode.

(f) to create a harmonious plasma cloud with low atomic particle chaos and turbulence by frequency matching the energy from our electromagnetic generator system to the atomic particle oscillation harmonics of the plasma cloud which coats and surrounds the activated incising transmitter tip.

(g) to create a harmonious plasma cloud with low atomic particle chaos and turbulence by power matching our electromagnetic generator system output power to the power requirements needed to stimulate and sustain a harmonious plasma cloud.

(h) to produce a tightly coupled, high efficiency transfer of the electromagnetic waveform generator energy into the plasma cloud surrounding and coating the activated incising transmitter tip thereby reducing the radiofrequency generator/amplifier output power needed to stimulate and maintain a harmonious plasma cloud surrounding the activated incising transmitter tip.

(i) to utilize the physics principle known as the Pinch Effect in order to concentrate, compress and contour the harmonious plasma cloud coating the activated incising transmitter tip.

(j) to employ the physics principle known as the Magnetic Bottle effect to trap and contain the harmonious plasma cloud and thereby eliminate the need of a solid matter confinement container to encase the plasma cloud. We thereby eliminate the need for a hollow retention chamber for plasma near the activated incising transmitter tip.

(k) to utilize the physical chemistry principle of Tunnelling to reflect the electromagnetic wave transmitted by the activated incising transmitter tip off of matter surrounding the harmonious plasma cloud and then back into the harmonious plasma cloud surrounding the activated incising transmitter tip. In this manner, we are employing the Tunnelling effect to create an electromagnetic shield which minimizes transmitted electromagnetic radiation from interacting and penetrating into matter outside of the intended path of incision. This acts to minimize the potential side effects of radiation exposure. Furthermore, this electromagnetic radiation reflected back into the plasma cloud acts to further energize the harmonious plasma cloud thereby further reducing the output energy required from the electromagnetic generator system.

(l) to use a harmonious plasma cloud condensed around the activated incising transmitter tip to focus the kinetic energy of the cutting plasma into a thinner cutting path in order to produce a discrete, clean incision into matter with minimal impact or side effects to matter outside of the intended path of incision.

(m) to produce an alternative to purely physical energy cutting techniques such as knives and blades, while also providing a more efficient, more effective, cleaner and less expensive approach than other alternate cutting modalities presently available, such as lasers.

DETAILED DESCRIPTION OF THE PREFERRED EMBODIMENTS

Our method of incising matter is different from all prior methods of incising matter. We employ an inexpensive electronic radiofrequency signal generator/amplifier system to produce a pulsed or continuous radiofrequency electromagnetic wave which is directed into an incisional handpiece and is then transmitted from an incising transmitter probe. Our incising probe is preferably a solid, non-hollow conductor, although a partial or completely hollow incising transmitter probe is acceptable. Our system is similar to a standard radio transmitter which is impedance matched to atmospheric air, whereas our system is impedance matched, frequency matched, power matched and tuned to a harmonious plasma cloud surrounding the activated incising transmitter electrode tip.

Plasma is the least abundant of the four types of matter to be found on earth, although it is the most abundant form of matter to be found in the universe. Examples of plasma on earth include: arc welding, spark plug arcs, neon lights, arcs around lightning discharges, and caustic plasma arcs seen in electrosurgery. Plasma is also used in fields such as semiconductor etching but is herein produced by expensive and high energy consumption systems such as lasers or elaborate plasma etching chambers.

Our system employs an inexpensive, electronic radiofrequency generator/amplifier system to produce and transmit a continuous or pulsed electromagnetic field from an activated incising transmitter probe. Individual parameters of this electromagnetic field generator system are largely determined by the atomic particle components along the interface of the transmitter incising probe and the matter to be incised. Our system utilizes the atoms along the incising transmitting probe interface to generate a plasma cloud as opposed to systems which require an ionizable gas to be injected into the field of incision and thereupon be energized and converted into plasma. Our incising transmitter probe is preferably linear or curvilinear in design; however, the shape of the transmitter tip electrode is not necessarily specific in design and may even have a loop design. Our system is impedance matched, frequency matched, and output power matched to generate and sustain a harmonious plasma cloud that coats the activated transmitter incising probe, thereby minimizing the classic plasma arcing occurring at the interface of the incising tip and the matter to be incised.

Arcing, per se, is a form of disharmonious plasma flow and represents uncontrolled, turbulent flow of ionized atomic particles in plasma that results in increased atomic particle chaos in the plasma. Merely reducing the cutting tip power does not by itself significantly improve the plasma harmony in as much as it does not greatly decrease the flow turbulence of the ionized atomic particles that make up a plasma arc. As with other forms of matter, plasma has a wide range of physical presentation including a wide range of temperature, density, flow characteristics, atomic particle components, etc. On earth, plasma arcing can be found in a number of areas such as welding arcs, spark plug arcs, lightening bolt arcs, neon lights and electrosurgical arcs. The high atomic particle turbulence in plasma arcs represents a form of atomic particle chaos, wherein the uncontrolled nature of the atomic particle chaos is caused by turbulent flow of the atomic particles in the plasma cloud. This form of plasma represents disharmonious plasma and results in excessive heating or a large quantity of energy spillover into matter outside of the intended path of incision. This energy spillover extending beyond the intended path of incision into matter results in energy exposure, thermal exposure and damage to surrounding matter. In this way, our invention minimizes plasma arcing by minimizing the atomic particle turbulence and chaos in the plasma cloud, and thereby acts to generate a harmonious plasma cloud.

As the electromagnetic field traverses the thin coating of harmonious plasma surrounding the activated transmitter incising probe, the electromagnetic field is slowly damped or decreased in amplitude. Finally, the electromagnetic field will pass completely through the plasma cloud and will encounter matter outside of the intended incision path which surrounds the cloud of incising plasma. According to the physical chemistry principle of Tunnelling, the generated electromagnetic wave then encounters a barrier to which it is not tuned nor impedance matched and thereby a large percentage of the total energy of the electromagnetic wave is reflected back into the harmonious plasma cloud. This reflected electromagnetic energy acts to further energize the molecular particles in the plasma cloud, thereby reducing the output energy which must be transmitted by the electromagnetic wave generator system. This process also serves to minimize the percentage of total electromagnetic radiation that penetrates into, that reacts with, and that presents potential radiation exposure damage to matter outside of the intended incision path.

The centripetal force of our generated magnetic field is used to control the distance between the atomic particles in the harmonious plasma cloud and the surface of the activated transmitter incising probe. To this end, the Pinch Effect which has been used for many years in fields such as plasma physics is employed in our system. In this way we are able to compress, contour, shape and control the harmonious plasma cloud with a solid or hollow transmitter incising probe. We then employ the Magnetic Bottle Effect used previously in fields such as nuclear physics to trap and contain the compressed plasma cloud without the need of solid matter containment vessels and thereby avoiding the requirement to employ hollow or cavity containing incising tip probes to trap and control plasma. Increasing the density of the atomic particles in the harmonious plasma cloud allows us to increase the plasma cloud power density thereby increasing the cutting efficiency and power of the plasma cloud.

Furthermore, compressing the plasma cloud causes a decrease in the cross sectional diameter of the plasma cloud thereby decreasing the width of the intended incision path as well as minimizing side effects or potential adverse impact on matter outside of the intended path of incision. Once the electromagnetic wave generator system has its power turned off, the energy level of the harmonious plasma cloud quickly decays to a point where the atomic particles comprising the plasma cloud cannot be sustained in the state of matter known as plasma.

Accordingly, the reader will see that employing a specifically tuned electromagnetic wave to generate a harmonious plasma which may have its shape and contour controlled allows us a more efficient, more controlled, less toxic, and more cost effective method of incising matter.

Although the description above contains many specifications, these should not be construed as limiting the scope of the invention but as merely providing illustrations of some of the presently preferred embodiments of this invention. Thus, the scope of the invention should be determined by the appended claims and the legal equivalents, rather than the examples given.

I claim:

1. A method of incision of matter using plasma, comprising the steps of:
    employing an electronic system comprising a radiofrequency signal generator and power amplifier,
    producing radiofrequency energy,
    feeding said radiofrequency energy into an active incising transmitter electrode tip,
    generating an electromagnetic field outward from the surface of said active incising transmitter electrode tip,
    creating a plasma cloud that coats said active incising transmitter electrode tip by the mechanism of activating atomic particles along an interface of said active incising transmitter tip and said matter that is to be incised without the need to inject ionizable gas into the space surrounding said active incising transmitter electrode tip,
    sustaining said plasma cloud by a high efficiency energy transfer from an electromagnetic wave to said atomic particles along said interface of said surface of said active incising transmitter electrode tip and said matter that is to be incised, and
    incising said matter by utilizing energy of said plasma cloud surrounding said active incising transmitter electrode tip to produce a safe, clean, efficient and effective incision in said matter.

2. The method of claim 1 wherein said step of feeding said radiofrequency includes a step of constructing said active incising transmitter electrode tip with electrically conductive or semi-conductive matter which is preferably a solid tip but may also be a hollow or a semi-hollow tip.

3. The method of claim 1 wherein said step of feeding said radiofrequency includes a step of constructing said active incising transmitter electrode tip with a preferably linear or curved-linear shape design, loop design, or non-specific shape design.

4. The method of claim 1 wherein step of generating an electromagnetic field includes a step of producing a continuous electromagnetic waveform.

5. The method of claim 1 wherein step of generating an electromagnetic field includes a step of producing a pulsed electromagnetic waveform.

6. The method of claim 1 wherein said steps of creating and sustaining said plasma cloud includes impedance matching, frequency matching, and power matching said radiofrequency energy from said radiofrequency signal generator and power amplifier to said plasma cloud coating said active incising transmitter electrode tip.

7. The method of claim 6 further comprising a step of producing a high efficiency, tightly coupled energy transfer from said radiofrequency energy from said radiofrequency signal generator and amplifier to said atomic particles in said plasma cloud along said surface of said incising transmitter electrode tip.

8. The method of claim 7 further comprising a step of matching the required output power of said radiofrequency signal generator and power amplifier to generate and sustain a harmonious plasma cloud.

9. The method of claim 6 further comprising a step of reducing turbulence and chaos of said atomic particles in said plasma cloud along said surface of said incising transmitter electrode tip.

10. The method of claim 9 further comprising a step of developing a harmonious plasma cloud which coats said surface of said incising transmitter electrode tip.

11. The method of claim 6 further comprising a step of allowing a high percentage of the total energy of said electromagnetic wave generated from said radiofrequency signal generator and power amplifier to transmit through said plasma cloud but subsequently have a high percentage of said total energy of said electromagnetic wave be reflected back into said plasma cloud when said electromagnetic wave reaches the interface between said plasma cloud and said matter that is to be incised, according to the Tunnelling effect of physical chemistry.

12. The method of claim 11 further comprising the step of allowing the reflected energy of said electromagnetic wave to further energize said plasma cloud, thereby further reducing the energy output required to be transmitted by said radiofrequency signal generator and power amplifier in order to generate and sustain said plasma cloud.

13. The method of claim 11 further comprising a step of shielding said matter surrounding a path of intended incision from said energy of said electromagnetic wave, thereby protecting said matter outside of said path of incision from radiation exposure.

14. The method of claim 1 wherein said step of sustaining said plasma cloud includes a step of using a transmitted magnetic wave to control the distance between said atomic particles in said plasma cloud and said surface of said active incising transmitter electrode tip.

15. The method of claim 14 further comprising a step of trapping, compressing, contouring, and controlling the shape and density of said plasma cloud by utilizing energy of said transmitted magnetic wave according to the Pinch Effect of physics.

16. The method of claim 15 further comprising a method of increasing the energy density of said plasma cloud while decreasing the cross sectional diameter of said plasma cloud and the width of said intended path of incision into matter.

17. The method of claim 14 further comprising a step of trapping and confining said plasma cloud without the need of a solid matter confinement or containment vessel or the need to inject said ionizable gas into said space surrounding said active incising transmitter tip by utilizing said transmitted magnetic wave according to the Magnetic Bottle Effect of physics.

18. The method of claim 1 wherein said step of incising said matter includes a step of selectively varying frequency and power of said electromagnetic wave according to the requirements of variations in said atomic particles comprising said plasma cloud as well as the ability to change the physical parameters of said plasma cloud.

* * * * *